United States Patent [19]

Frantzich et al.

[11] 4,357,935
[45] Nov. 9, 1982

[54] DRY METHOD OF MAKING A DRY SOCKET DRESSING

[75] Inventors: William P. Frantzich, Wayzata; Garry R. Persons, Edina, both of Minn.

[73] Assignee: C. R. Canfield & Company, Inc., Edina, Minn.

[21] Appl. No.: 206,281

[22] Filed: Nov. 12, 1980

[51] Int. Cl.³ .............................................. A61L 15/00
[52] U.S. Cl. ..................................... 128/156; 128/155
[58] Field of Search ........................ 128/155, 156, 260; 424/16, 19; 427/2, 430.1, 445

[56] References Cited

U.S. PATENT DOCUMENTS

| | | | |
|---|---|---|---|
| 3,339,546 | 5/1967 | Chen | 128/156 |
| 3,696,811 | 10/1972 | Chen | 128/156 |
| 3,803,300 | 4/1974 | Pospischil | 128/156 |
| 4,036,227 | 7/1977 | Zaffaroni | 128/260 |
| 4,039,653 | 8/1977 | Defoney et al. | 128/260 |
| 4,292,299 | 9/1981 | Suzuki et al. | 128/156 |

FOREIGN PATENT DOCUMENTS 1561891 8/1958 Canada ................................ 128/156

*Primary Examiner*—Richard J. Apley
*Assistant Examiner*—T. J. Wallen
*Attorney, Agent, or Firm*—Williamson, Bains, Moore & Hansen

[57] ABSTRACT

A dressing for use in treating dry socket syndrome resulting from tooth extraction includes a gauze strip impregnated with a gelatinous material containing petrolatum, emulsifiers and an analgesic substance such as eugenol. In the process of making and packaging the dry socket dressing, a strip of gauze is unrolled from a roll and passed through a bath containing a gelatinous material at a rate to permit a six-inch length of gauze to incorporate approximately two grams of gelatinous material. The impregnated strip is then cut into predetermined lengths and thereafter packaged in a transparent, sealed envelope. The package containing the dry socket dressing is then treated with gamma radiation to sterilize the dressing and interior of the envelope.

3 Claims, 4 Drawing Figures

U.S. Patent  Nov. 9, 1982  4,357,935
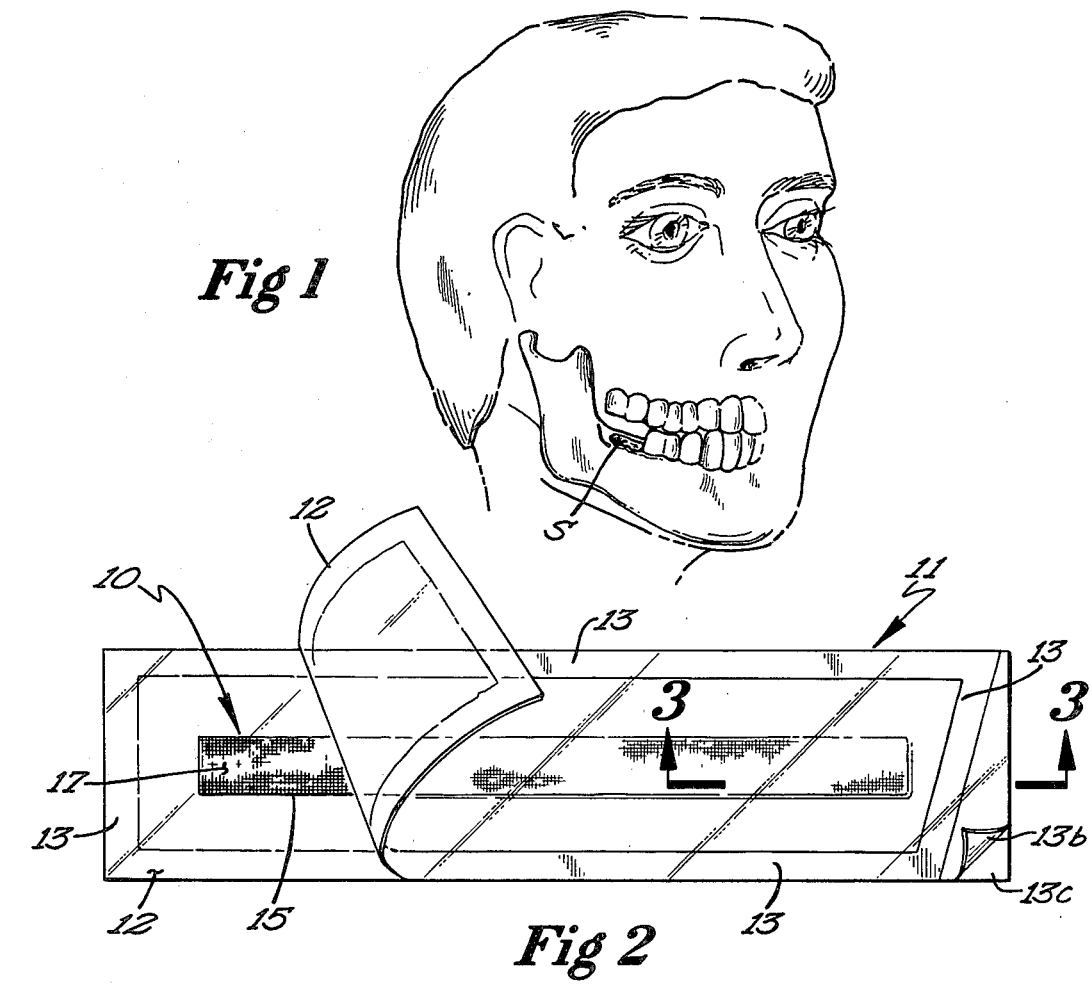
Fig 1
Fig 2
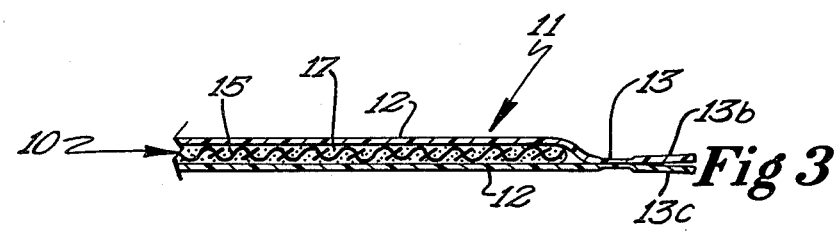
Fig 3
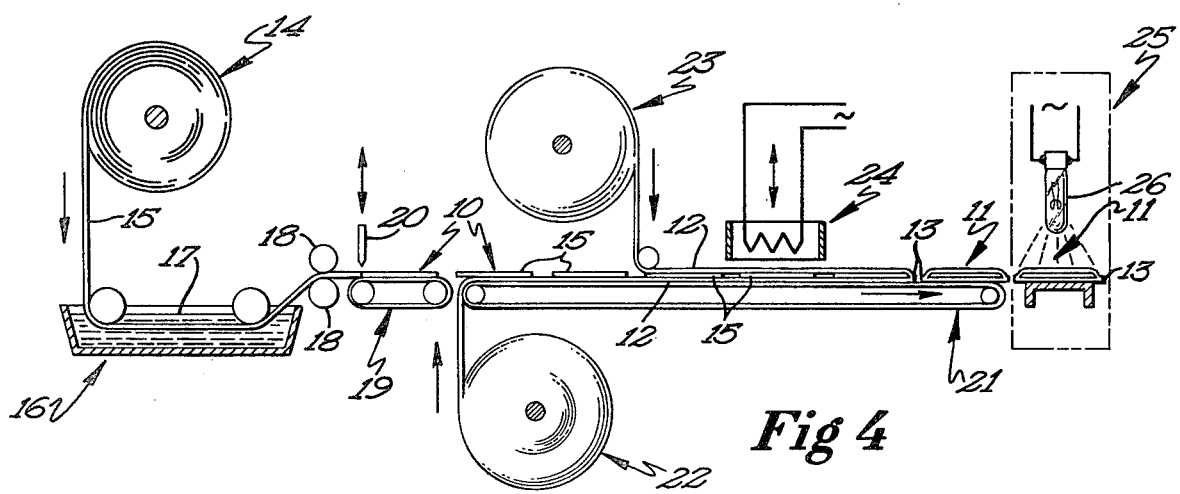
Fig 4

DRY METHOD OF MAKING A DRY SOCKET DRESSING

SUMMARY OF THE INVENTION

This invention relates to a dry socket dressing for treating dry socket syndrome resulting from tooth extractions.

It has been found that approximately 10% of mandibular third molar tooth extractions result in dry socket syndrome, a condition in which the area from which the tooth was removed fails to heal properly. As a result of the condition, the patient suffers substantial pain.

A standard practice by dentists and oral surgeons in treating this condition is to pack the dry socket with a piece of medicated gauze to promote healing and to relieve pain. These packings are usually extemporaneously prepared by the dentists or associates in his office or clinic. Usually, a length of gauze is immersed in a jar containing a mixture of ointment consisting of a gelatinous material along with certain medicaments. As the packing is needed, the dentist extracts gauze from the jar and snips off a desired length. However, such packings have not been sterilized, are messy to work with, and tend to dry out with age.

It is therefore, the general object of this invention to provide a sterile, pre-packaged dry socket dressing and process for preparing the same.

A more specific object of this invention is to provide a process for preparing a dry socket dressing in which a strip of gauze is unwound from a roll, passed through an impregnated gelatinous bath containing a medicament, cut into predetermined lengths, packaged in a heat-sealed inert transparent package, and then treating the packaged dry socket dressing with gamma radiation to sterilize the package and its contents.

These and other objects and advantages of this invention will more fully appear from the following description made in connection with the accompanying drawings, wherein like reference characters refer to the same or similar parts throughout the several views.

FIGURES OF THE DRAWINGS

FIG. 1 is a view of the patient following a molar extraction in which the dry socket dressing is to be used;

FIG. 2 is a top plan view of the packaged dry socket dressing;

FIG. 3 is a fragmentary cross-sectional view taken approximately along lines 3—3 of FIG. 2 and looking in the direction of the arrows; and FIG. 4 is a diagrammatic illustration of the steps in carrying out the novel process for preparing the packaged dry socket dressing.

DESCRIPTION OF THE PREFERRED EMBODIMENT OF THE INVENTION

Referring now to the drawings and more particularly to FIG. 2, it will be seen that one embodiment of the novel dry socket dressing, designated generally by the reference numeral 10 is thereshown. The dry socket dressing 10 is contained within a package or envelope 11 and which is preferably formed of an inert, transparent packaging material, such as polyethylene. In the embodiment shown, the package is comprised of substantially identical upper and lower rectangular panels 12 which are sealingly secured together by a peripheral heat seal 13. It will be noted that the heat seal along one transverse edge portion of the package 11 is spaced from the edge to define a flap 13b and 13c which permits the package to be peeled open.

In the embodiment shown, the dry socket dressing 10 is formed of an impregnated gauze strip whose dimensions are 0.64 cm. by 15.3 cm. ($\frac{1}{4}"\times 6"$). The package 11 is slightly larger than the dry socket dressing, and in the embodiment it is preferred that the package be of rectangular configuration having dimensions 3.8 cm. by 17.8 cm. ($1\frac{1}{2}"\times 7"$). The interior of the package and the dry socket dressing are sterile as a result of having been subjected to 2.5 Mrads of gamma radiation although other possible systems of sterilization might be used.

In the process of making and producing the packaged dry socket dressing, a roll 14 of the gauze will be mounted so that the gauze may continuously unwind from the roll. The gauze may be either a natural fabric, such as cotton, or a synthetic fabric, such as polyester. Other materials may be used and their densities and weaves may also vary. Therefore, the term, gauze, used herein may include natural and synthetic fabrics having a variety of weaves and densities. The gauze strip 15 is preferably 0.64 cm wide ($\frac{1}{4}"$) and will be moved in a predetermined path of travel so that the strip of gauze 15 first passes through a container 16 containing a predetermined amount of an impregnating bath 17 therein. Any suitable means may be used for moving the strip 15 of gauze in its predetermined movement such as the driving rolls 18. The dwell time for the strip of gauze material in the impregnating bath 17 is sufficient so that a length of gauze material 15.3 cm (6") incorporates approximately two grams of the material in the bath. It is important to maintain control of the temperature of the impregnating bath in order to obtain the desired amount of material on the strip of gauze. Alternate methods of impregnation are also possible.

After impregnation, the gauze strip 15 is continued in its path of travel by a conveyor 19 or automated device and is then cut into the desired lengths, preferably 15.3 cm, by a cutting device 20. The dry socket dressings 10 are then continued in their path of travel by a suitable conveyor 20 upon which is supported a sheet of the packaging material. The impregnated strips which form the dry socket dressing 10 are disposed upon the lower panel 12 of the package which is unwound from a roll 22 of the packaging material. Thereafter, a sheet of packaging material is unwound from a roll 23 and forms the upper panel 12 for the package for the dry socket dressing. The edges of the panels are heat sealed by heat sealer 24 and cut to form each package. The entire package containing the dry socket dressing is then subjected to a radiation unit 25 which emits gamma radiation to sterilize the interior of the package and dry dressing itself. Since the dry socket dressing is completely sealed from the exterior and is sterile, the dry socket dressing has a long shelf life. The dry socket dressing is ready for use and when the package is opened, it may be readily grasped at one end using forceps for placing the dressing in a patient's dry socket.

In the embodiment shown, the impregnating bath is formed of a suitable ointment for rendering the strip of gauze soft and pliant so that it will not present a stiff, angular surface to cause discomfort to the patient when the impregnated strip is packed into the painful socket. The ointment may either be an absorbent, hydrophilic type sold under the trademark of Aquaphor ® by Beiersdorf, Inc., South Norwalk, Connecticut, or may be hydrophobic such as white petrolatum U.S.P. It is also preferred that the bath also contain an analgesic, local anesthetic, antibiotic, and/or other medicament such as clove oil, pine oil or isopropyl alcohol. Emulsifiers are also used so that the medicament(s) is/are maintained in a homogenous suspension in the ointment.

An example of the impregnating bath which is found to be especially suitable for impregnating the gauze consists of approximately 65% to 95%, by weight of white petrolatum, U.S.P. approximately 1% to 25% by weight of eugenol, U.S.P., approximately 0.75% by weight of a commercial emulsifier (polyoxyethylene 20 sorbitan monostearate), sold under the trademark Tween 60 by I.C.I. Americans, Inc., Wilmington, Delaware, and approximately 4.25% by weight of another commercial emulsifier (mono and diglycerides and propylene glycol, vicosity 150 $c_p f$ sold under the trademark Arlacel 186 by I.C.I. Americans, Inc., the range of the emulsifier is 1% to 15% by weight. The white petroleum and Arlacel 186 are mixed and heated to the same temperature in another container. The eugenol-Tween 60 solution is then poured into the container containing the white petrolatum-Arlacel 186 solution, mixed briskly, and then allowed to cool approximately 120° F. Then the liquid gauze was moved through the bath. While it is preferred that the impregnation bath be cooled to approximately 120° F., before the gauze strip is introduced into the bath, acceptable results may be obtained by moving the strip through the bath as long as the temperature thereof is within the range of 105° to 130°.

It has been found that dry socket packings approximately having dimensions of 0.64 cm. by 15.3 cm. and containing white petrolatum and eugenol with suitable surfactants function well in treating dry sockets. The sterile, ready-to-use availability of the dry socket packing also obviates the need of extemporaneously preparing such packings by the dentist or associates.

Thus, it will be seen that I have provided a novel dry socket dressing which is not only sterile and stable, but one which provides a ready-to-use, efficient manner of treating dry socket syndrome.

It is anticipated that various changes can be made in the size, shape, ingredient(s), and construction of the dry socket dressing disclosed herein without departing from the spirit of the invention as defined in the following claims.

What is claimed is:

1. A process for making a dressing for treating dry sockets resulting from tooth extractions, comprising:
   combining a predetermined amount of ointment and a predetermined amount of an emulsifier, and heating said mixture to a temperature within the range of approximately 135° to 150° F., adding a mixture containing a predetermined amount of a liquid analgesic material and an emulsifier to said first mixture to form an impregnation bath containing approximately 75% to 95% by weight of ointment and approximately 1% to 25% by weight of emulsifiers and analgesic material,
   cooling said impregnation bath to a temperature of approximately 105° to 125° F.,
   moving an elongate, narrow strip of gauze through said bath to permit a predetermined amount of the impregnation bath material to impregnate and adhere to the gauze strip,
   cutting the impregnated gauze into strips of predetermined lengths,
   packaging said strips in a transparent package formed of an inert plastic which is sealed from the exterior,
   and exposing the sealed package containing the impregnated gauze to gamma radiation to sterilize the impregnated gauze strips and the interior of the package.

2. The process as defined in claim 1 wherein said impregnation bath contains approximately 1% to 25% by weight of eugenol.

3. The process as defined in claim 1 wherein said narrow strips of gauze are moved through said impregnation bath at a rate of approximately 2 grams of the impregnation bath material to impregnate and adhere a gauze strip unit having an area within a range of approximately 5 to 25 square cm.

* * * * *